(12) United States Patent
Ballinger et al.

(10) Patent No.: US 6,485,920 B1
(45) Date of Patent: Nov. 26, 2002

(54) GROWTH FACTOR ANTAGONIST MATERIALS AND METHODS

(75) Inventors: Dennis G. Ballinger, Menlo Park, CA (US); Julie Reeder Montgomery, Los Gatos, CA (US)

(73) Assignee: Hyseq Inc., Sunnyvale, CA (US)

( * ) Notice: Subject to any disclaimer, the term of this patent is extended or adjusted under 35 U.S.C. 154(b) by 0 days.

(21) Appl. No.: 10/090,190

(22) Filed: Mar. 4, 2002

Related U.S. Application Data

(62) Division of application No. 09/370,398, filed on Aug. 6, 1999, now Pat. No. 6,423,682.

(51) Int. Cl.[7] .............................................. G01N 33/53
(52) U.S. Cl. ...................................... 435/7.21; 435/7.1
(58) Field of Search ................................ 435/7.1, 7.21

(56) References Cited

FOREIGN PATENT DOCUMENTS

WO  WO 98/20032  5/1998
WO  WO 00/15781  3/2000

OTHER PUBLICATIONS

Hacohen et al, Sprouty encodes a novel antagonist of FGF signaling that patterns apical branching of the drosophila airways. Cell, 92:253–263, 1998.*
Kramer et al, Sprouty: a common antagonist of FGF and EGF signaling pathways in drosophila. Development, 126:2515–2525, 1999.*
Casci et al, Sprouty, an intracellular inhibitor of Ras signaling. Cell, 96:655–665, 1999.*
Lee et al, Inhibition of angiogenesis by a mouse sprouty protein. J. Biol. Chem. 276:4128–4133, 2001.*
Peer Bork and Eugene V. Koonin, Predicting functions from protein sequences—where are the bottlenecks? Nature Genetics 18:313–318, 1998.*
Casci et al., *Sprouty, an intracellular Inhibitor of Ras Signaling*, Cell 96(5): 655–665 (Mar. 1999).
de Maximy et al., *Cloning and Expression Pattern of a Mouse Homologue of Drosophila Sprouty in the Mouse Embryo*, Mechanisms of Development 81: 213–216 (1999).
Hacohen et al., *Sprouty Encodes a Novel Antagonist of FGF Signaling that Patterns Apical Branching of the Drosophila Airways*, Cell 92: 253–263 (Jan. 23, 1998).
Impagnatiello et al., *Mammalian Sprouty–1 and –2 Are Membrane–Anchored Phosphoprotein Inhibitors of Growth Factor Signaling in Endothelial Cells*, The Journal of Cell Biology 152(5): 1087–1098 (Mar. 5, 2001).

Kramer et al., *Sprouty: a Common Antagonist of FGF and EGF Signaling Pathways in Drosophlla*, Development 126: 2515–2525 (May 1999).
Lee et al., *Inhibition of Angiogenesis by a Mouse Sprouty Protein*, The Journal of Biological Chemistry 276(6): 4128–4133 (Feb. 9, 2001).
Metzger et al., *Genetic Control of Branching Morphogenesis*, Science 284: 1635–1639 (Jun. 4, 1999).
Minowada et al., *Vertebrate Sprouty Genes are Induced by FGF Signaling and can Cause Chondrodysplasia When Overexpressed*, Development 126: 4465–4475 (Sep. 27, 1999).
Placzek and Skaer, *Airway Patterning: A Paradigm for Restricted Signaling*, Current Biology 9: R506–R510 (1990).
Reich et al., *Sprouty is a General Inhibitor of Receptor Tyrosine Kinase Signaling*, Development 126: 4139–4147 (Aug. 23, 1999).
Tefft et al., *Conserved Function of mSpry–2, a Murine Homolog of Drosophila Sprouty, Which Negatively Moduletes Respiratory Organogenesis*, Current Biology 9:219–222 (1999).
Wong et al., *Evidence for Direct Interaction Between Sprouty and Cbl*, The Journal of Biological Chemistry 276(8): 5866–5875 (Feb. 23, 2001).
Lim et al., *Sprouty Proteins Are Targeted to Membrane Ruffles upon Growth Factor Receptor Tyrosine Kinase Activation*, The Journal of Biological Chemistry 275(42): 32837–32845 (Oct. 20, 2000).
Sasaki et al., *Identification of a Dominant Negative Mutant of Sprouty That Potentiates Fibroblast Growth Factor–but Not Epldermal Growth Factor–induced ERK Activation*, The Journal of Biological Chemistry 276(39): 36804–36808 (Sep. 28, 2001).
Yigzaw et al., *The C Terminus of Sprouty Is Importent for Modulation of Cellular Migration and Proliferation*, The Journal of Biological Chemistry 276(25): 22742–22742–22747 (Jun. 22, 2001).

* cited by examiner

Primary Examiner—Elizabeth Kemmerer
Assistant Examiner—Ruixiang Li
(74) Attorney, Agent, or Firm—Marshall, Gerstein & Borun

(57) ABSTRACT

The present invention provides nucleic acids encoding Sprouty related human growth factor antagonist proteins (designated FGFAn–Hy), the polypeptides encoded by these nucleic acids and uses of these and related products.

2 Claims, 3 Drawing Sheets

Fig. 1A

```
                10              20              30              40
     MEPPIP--QSA-PLTPNSVMVQPLLDSRMSHSRLQHPLTI           CG165 (SEQ ID NO:2)
 1   MEARAQSGNGSQPLLQTPRDGGRQRGEPDPRDALTQQVHV           human sprouty-2 (SEQ ID NO:3)
 1   --------------------------------------            human sprouty-1 (SEQ ID NO:4)
 1   MEPPVP--QSSVPVNPSSVMVQPLLDSRAPHSRLQHPLTI           mouse sprouty-4 (SEQ ID NO:5)
 1   MEARAQSGNGSQPLLQTAHDSGRQRGEPDPRDALTQQVHV           mouse sprouty-2 (SEQ ID NO:6)
 1   ---------------------------------------P          human sprouty-3 (SEQ ID NO:7)

50              60              70              80
 38  LPIDQVKTSHVENDYIDNPSLALTTGPK------------           CG165 (SEQ ID NO:2)
 41  LSLDQIRAIRNTNEYTEGPTVVPRPGLKPAPRPSTQHKHE           human sprouty-2 (SEQ ID NO:3)
 1   ---------------------------------------            human sprouty-1 (SEQ ID NO:4)
 39  LPIDQMKTSHVENDYIDNPSLAPATGPK------------           mouse sprouty-4 (SEQ ID NO:5)
 41  LSLDQIRAIRNTNEYTEGPTVVPRPGLKPAPRPSTQHKHE           mouse sprouty-2 (SEQ ID NO:6)
 2   LPLDQ----------------------------------            human sprouty-3 (SEQ ID NO:7)

90             100             110             120
 66  RTRG----GAPELAPTPARCDQDVTHHW----ISFSGRP            CG165 (SEQ ID NO:2)
 81  RLHGLPEHRQPPRLQHSQVHSSARAPLSRSISTVSSGSRS           human sprouty-2 (SEQ ID NO:3)
 1   ---------------------------------------            human sprouty-1 (SEQ ID NO:4)
 67  RPRG----GPPELAPTPARCDQDITHHW----ISFSGRP            mouse sprouty-4 (SEQ ID NO:5)
 81  RLHGLPEHRQPPRLQPSQVHSS-RAPLSRSISTVSSGSRS           mouse sprouty-2 (SEQ ID NO:6)
 7   ---------------------------------------            human sprouty-3 (SEQ ID NO:7)
```

Fig. 1B

```
              130       140       150       160
 97  SSVSSSSTSSDQRLLDH-MAPPPVADQASP--RAVRIQP            CG165           (SEQ ID NO:2)
121  STRTSTSSSSEQRLLGSSFSSGPVA-DGI-----IRVQP            human sprouty-2 (SEQ ID NO:3)
  1  ---------------------------------IRVQP            human sprouty-1 (SEQ ID NO:4)
 98  SSVSSSSTSSDQRLLDH-MAPPPVAEQASP--RAVRLQP            mouse sprouty-4 (SEQ ID NO:5)
120  STRTSTSSSSEQRLLGPSFSHGPAAADGI-----IRVQP            mouse sprouty-2 (SEQ ID NO:6)
  7  --------RLLA-SITPSPSGQSIIRTQPGAGVHP                human sprouty-3 (SEQ ID NO:7)

170       180       190       200
134  KVVHCQPLDLKGPAVPPELDKHFLLCEACGKCKCKECASP           CG165           (SEQ ID NO:2)
155  KSEL-KPGELK-PLSKEDLGLHAYRCEDCGKCKCKECTYP           human sprouty-2 (SEQ ID NO:3)
  1  ------------------CEQCGKCKCGECTAP                  human sprouty-1 (SEQ ID NO:4)
135  KVVHCKPLDLKGPTAPPELDKHFLLCEACGKCKCKECASP           mouse sprouty-4 (SEQ ID NO:5)
155  KSEL-KPGDIK-PLSKDDLGLHAYRCEDCGKCKCKECTYP           mouse sprouty-2 (SEQ ID NO:6)
 33  KADGALKGEAEQSAGHP--SEHLFICEECGRCKCVPCTAA           human sprouty-3 (SEQ ID NO:7)

210       220       230       240
174  RTLPSCWVCNQECLCSAQTLVNYGTCMCLVQGIFYHCTNE           CG165           (SEQ ID NO:2)
193  RPLPSDWICDKQCLCSAQNVIDYGTCVCCVKGLFYHCSND           human sprouty-2 (SEQ ID NO:3)
 16  RTLPSCLACNRQCLCSAESMVEYGTCMCLVKGIFYHCSND           human sprouty-1 (SEQ ID NO:4)
175  RTLPSCWVCNQECLCSAQTLVNYGTCMCLVQGIFYHCTNE           mouse sprouty-4 (SEQ ID NO:5)
193  RPLPSDWICDKQCLCSAQNVIDYGTCVCCVKGLFYHCSND           mouse sprouty-2 (SEQ ID NO:6)
 71  RPLPSCWLCNQRCLCSAESLLDYGTCLCCV                     human sprouty-3 (SEQ ID NO:7)
```

Fig. 1C

```
     250        260        270       280
214 DDEGSCADHPCSCSRSNCCARWSFMGALSVVLPCLLCYLP  CG165          (SEQ ID NO:2)
233 DE-DNCADNPCSCSQSHCCTRWSAMGVMSLFLPCLLCYLP  human sprouty-2 (SEQ ID NO:3)
 56 DEGDSYSDNPCSCSQSHCCSRYLCMGAMSLFLPCLLCYPP  human sprouty-1 (SEQ ID NO:4)
215 DDEGSCADHPCSCSGSNCCARWSFMGALSVVLPCLLCYLP  mouse sprouty-4 (SEQ ID NO:5)
233 DE-DNCADNPCSCSQSHCCTRWSAMGVMSLFLPCLWCYLP  mouse sprouty-2 (SEQ ID NO:6)
100 -                                         human sprouty-3 (SEQ ID NO:7)

290        300        310       320
254 ATGCVKLAQRGYDRLRRPGCRCKHTNSVICKAASGDAKTS  CG165          (SEQ ID NO:2)
272 AKGCLKLCQGCYDRVNRPGCRCKNSNTVCCKVPTVPPRN-  human sprouty-2 (SEQ ID NO:3)
 96 AKGCLKLCRRCYDWIHRPGCRCKNSNTVYCKLESCPSRG-  human sprouty-1 (SEQ ID NO:4)
255 ATGCVKLAQRGYDRLRRPGCRCKHTNSVICKAASGDTKTS  mouse sprouty-4 (SEQ ID NO:5)
272 AKGCLKLCQGCYDRVNRPGCRCKNSNTVCCKVPTVPPRN-  mouse sprouty-2 (SEQ ID NO:6)
100                                           human sprouty-3 (SEQ ID NO:7)

294 RPDKPF  CG165          (SEQ ID NO:2)
311 -FEKPT  human sprouty-2 (SEQ ID NO:3)
135 -QGKPS  human sprouty-1 (SEQ ID NO:4)
295 RSDKPF  mouse sprouty-4 (SEQ ID NO:5)
311 -FEKPT  mouse sprouty-2 (SEQ ID NO:6)
100         human sprouty-3 (SEQ ID NO:7)
```

SEQUENCE LISTING

```
<160> NUMBER OF SEQ ID NOS: 13

<210> SEQ ID NO 1
<211> LENGTH: 1662
<212> TYPE: DNA
<213> ORGANISM: Homo sapiens
<220> FEATURE:
<221> NAME/KEY: CDS
<222> LOCATION: (211)..(1107)

<400> SEQUENCE: 1
aggtagcgag ctgagctgac agcgcggagc tggcgctgtg gagcgcaggg agccttgccg      60
gttcctccga ccggcgtctg cgagtacagc ggcggctaac ctgccccggc ttcaggattt     120
acacagacgt ggggcgatgc ttgtgaccct gcagctcctc aaaggcccct agaagcctgt     180
ttctccgtac agtccaggac ctccagcccc atg gag ccc ccg atc cca cag agc     234
                                   Met Glu Pro Pro Ile Pro Gln Ser
                                     1               5 gcc ccc ttg act ccc aac tca gtc atg gtc cag ccc ctt ctt gac agc     282
Ala Pro Leu Thr Pro Asn Ser Val Met Val Gln Pro Leu Leu Asp Ser
     10                  15                  20 cgg atg tcc cac agc cgg ctc cag cac cca ctc acc atc cta ccc att     330
Arg Met Ser His Ser Arg Leu Gln His Pro Leu Thr Ile Leu Pro Ile
 25                  30                  35                  40
```

-continued

| | |
|---|---|
| gac cag gtg aag acc agc cat gtg gag aat gac tac ata gac aac cct<br>Asp Gln Val Lys Thr Ser His Val Glu Asn Asp Tyr Ile Asp Asn Pro<br>               45                     50                    55 | 378 |
| agc ctg gcc ctg acc acc ggc cca aag cgg acc cgg ggc ggg gcc cca<br>Ser Leu Ala Leu Thr Thr Gly Pro Lys Arg Thr Arg Gly Gly Ala Pro<br>               60                     65                    70 | 426 |
| gag ctg gcc ccg acg ccc gcc cgc tgt gac cag gat gtc acc cac cat<br>Glu Leu Ala Pro Thr Pro Ala Arg Cys Asp Gln Asp Val Thr His His<br>               75                     80                    85 | 474 |
| tgg atc tcc ttc agc ggg cgc ccc agc tct gtg agc agc agc agc<br>Trp Ile Ser Phe Ser Gly Arg Pro Ser Ser Val Ser Ser Ser Ser Ser<br>     90                     95                    100 | 522 |
| aca tcc tct gac caa cgg ctc tta gac cac atg gca cca cca ccc gtg<br>Thr Ser Ser Asp Gln Arg Leu Leu Asp His Met Ala Pro Pro Pro Val<br>105                 110                 115                120 | 570 |
| gct gac cag gcc tca cca agg gct gtg cgc atc cag ccc aag gtg gtc<br>Ala Asp Gln Ala Ser Pro Arg Ala Val Arg Ile Gln Pro Lys Val Val<br>               125                 130                135 | 618 |
| cac tgc cag ccg ctg gac ctc aag ggc ccg gcg gtc cca ccc gag ctg<br>His Cys Gln Pro Leu Asp Leu Lys Gly Pro Ala Val Pro Pro Glu Leu<br>             140                 145                150 | 666 |
| gac aag cac ttc ttg ctg tgc gag gcc tgt ggg aag tgt aaa tgc aag<br>Asp Lys His Phe Leu Leu Cys Glu Ala Cys Gly Lys Cys Lys Cys Lys<br>          155                 160                165 | 714 |
| gag tgt gca tcc ccc cgg acg ttg cct tcc tgc tgg gtc tgc aac cag<br>Glu Cys Ala Ser Pro Arg Thr Leu Pro Ser Cys Trp Val Cys Asn Gln<br>170                 175                 180 | 762 |
| gag tgc ctg tgc tca gcc cag act ctg gtc aac tat ggc acg tgc atg<br>Glu Cys Leu Cys Ser Ala Gln Thr Leu Val Asn Tyr Gly Thr Cys Met<br>185                 190                 195                200 | 810 |
| tgt ttg gtg cag ggc atc ttc tac cac tgc acg aat gag gac gat gag<br>Cys Leu Val Gln Gly Ile Phe Tyr His Cys Thr Asn Glu Asp Asp Glu<br>               205                 210                215 | 858 |
| ggc tcc tgc gct gac cac ccc tgc tcc tgc tcc cgc tcc aac tgc tgc<br>Gly Ser Cys Ala Asp His Pro Cys Ser Cys Ser Arg Ser Asn Cys Cys<br>             220                 225                230 | 906 |
| gcc cgc tgg tcc ttc atg ggt gct ctc tcc gtg gtg ctg ccc tgc ctg<br>Ala Arg Trp Ser Phe Met Gly Ala Leu Ser Val Val Leu Pro Cys Leu<br>          235                 240                245 | 954 |
| ctc tgc tac ctg cct gcc acc ggc tgc gtg aag ctg gcc cag cgt ggc<br>Leu Cys Tyr Leu Pro Ala Thr Gly Cys Val Lys Leu Ala Gln Arg Gly<br>250                 255                 260 | 1002 |
| tac gac cgt ctg cgc cgc cct ggt tgc cgc tgc aag cac acg aac agc<br>Tyr Asp Arg Leu Arg Arg Pro Gly Cys Arg Cys Lys His Thr Asn Ser<br>265                 270                 275                280 | 1050 |
| gtc atc tgc aaa gca gcc agc ggg gat gcc aag acc agc agg ccc gac<br>Val Ile Cys Lys Ala Ala Ser Gly Asp Ala Lys Thr Ser Arg Pro Asp<br>             285                 290                295 | 1098 |
| aag cct ttc tgacagtttg tgtcgaagcc ccagtgctct gcctggaaac<br>Lys Pro Phe | 1147 |
| ctggttctct tctgacatct aagaagactg cagcaaggtc agaggtttta gcctcctgag | 1207 |
| gctgaccttg ctagtctgcc cactccctac ccccagcttc ggaaaataca gagaccacca | 1267 |
| ccacgtaccc tgtattcccc aagatgatga agaagcactt tggggctttt ttcagggtc | 1327 |
| ctgaaacttt gtgtcaaaca gacaatgcag gggcagggtg tggtttgggg ggaaattttt | 1387 |
| cttttttcaga agacagaaca cagatgtgga cacatatccg gaaactgcag ctgcttgaat | 1447 |
| gccttcccag ccctccttc tccctccctc cctccgcccc cccttcctc ttttccattg | 1507 |

```
tctttggcac tcacaggagc tagctgcctg ggaggaattg ctaactgagt accagggtac   1567
ctttaaagaa gaccttgga gtcttctata ccttcttctc cttccccatc tcactccacc   1627
ccactttgtc cctgatgtct tggggaaggt gtaga                              1662
```

<210> SEQ ID NO 2
<211> LENGTH: 299
<212> TYPE: PRT
<213> ORGANISM: Homo sapiens

<400> SEQUENCE: 2

```
Met Glu Pro Pro Ile Pro Gln Ser Ala Pro Leu Thr Pro Asn Ser Val
 1               5                  10                  15

Met Val Gln Pro Leu Leu Asp Ser Arg Met Ser His Ser Arg Leu Gln
                20                  25                  30

His Pro Leu Thr Ile Leu Pro Ile Asp Gln Val Lys Thr Ser His Val
            35                  40                  45

Glu Asn Asp Tyr Ile Asp Asn Pro Ser Leu Ala Leu Thr Thr Gly Pro
        50                  55                  60

Lys Arg Thr Arg Gly Gly Ala Pro Glu Leu Ala Pro Thr Pro Ala Arg
65                  70                  75                  80

Cys Asp Gln Asp Val Thr His His Trp Ile Ser Phe Ser Gly Arg Pro
                85                  90                  95

Ser Ser Val Ser Ser Ser Ser Thr Ser Ser Asp Gln Arg Leu Leu
                100                 105                 110

Asp His Met Ala Pro Pro Val Ala Asp Gln Ala Ser Pro Arg Ala
            115                 120                 125

Val Arg Ile Gln Pro Lys Val Val His Cys Gln Pro Leu Asp Leu Lys
        130                 135                 140

Gly Pro Ala Val Pro Pro Glu Leu Asp Lys His Phe Leu Leu Cys Glu
145                 150                 155                 160

Ala Cys Gly Lys Cys Lys Cys Lys Glu Cys Ala Ser Pro Arg Thr Leu
                165                 170                 175

Pro Ser Cys Trp Val Cys Asn Gln Glu Cys Leu Cys Ser Ala Gln Thr
            180                 185                 190

Leu Val Asn Tyr Gly Thr Cys Met Cys Leu Val Gln Gly Ile Phe Tyr
        195                 200                 205

His Cys Thr Asn Glu Asp Asp Glu Gly Ser Cys Ala Asp His Pro Cys
    210                 215                 220

Ser Cys Ser Arg Ser Asn Cys Cys Ala Arg Trp Ser Phe Met Gly Ala
225                 230                 235                 240

Leu Ser Val Val Leu Pro Cys Leu Leu Cys Tyr Leu Pro Ala Thr Gly
                245                 250                 255

Cys Val Lys Leu Ala Gln Arg Gly Tyr Asp Arg Leu Arg Pro Gly
            260                 265                 270

Cys Arg Cys Lys His Thr Asn Ser Val Ile Cys Lys Ala Ala Ser Gly
        275                 280                 285

Asp Ala Lys Thr Ser Arg Pro Asp Lys Pro Phe
    290                 295
```

<210> SEQ ID NO 3
<211> LENGTH: 315
<212> TYPE: PRT
<213> ORGANISM: Homo sapiens

<400> SEQUENCE: 3

```
Met Glu Ala Arg Ala Gln Ser Gly Asn Gly Ser Gln Pro Leu Leu Gln
 1               5                  10                  15

Thr Pro Arg Asp Gly Gly Arg Gln Arg Gly Glu Pro Asp Pro Arg Asp
            20                  25                  30

Ala Leu Thr Gln Gln Val His Val Leu Ser Leu Asp Gln Ile Arg Ala
        35                  40                  45

Ile Arg Asn Thr Asn Glu Tyr Thr Glu Gly Pro Thr Val Val Pro Arg
    50                  55                  60

Pro Gly Leu Lys Pro Ala Pro Arg Pro Ser Thr Gln His Lys His Glu
65                  70                  75                  80

Arg Leu His Gly Leu Pro Glu His Arg Gln Pro Pro Arg Leu Gln His
                85                  90                  95

Ser Gln Val His Ser Ser Ala Arg Ala Pro Leu Ser Arg Ser Ile Ser
            100                 105                 110

Thr Val Ser Ser Gly Ser Arg Ser Ser Thr Arg Thr Ser Thr Ser Ser
        115                 120                 125

Ser Ser Ser Glu Gln Arg Leu Leu Gly Ser Ser Phe Ser Ser Gly Pro
130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255

Gly Val Met Ser Leu Phe Leu Pro Cys Leu Trp Cys Tyr Leu Pro Ala
            260                 265                 270

Lys Gly Cys Leu Lys Leu Cys Gln Gly Cys Tyr Asp Arg Val Asn Arg
        275                 280                 285

Pro Gly Cys Arg Cys Lys Asn Ser Asn Thr Val Cys Cys Lys Val Pro
    290                 295                 300

Thr Val Pro Pro Arg Asn Phe Glu Lys Pro Thr
305                 310                 315

<210> SEQ ID NO 4
<211> LENGTH: 139
<212> TYPE: PRT
<213> ORGANISM: Homo sapiens

<400> SEQUENCE: 4

Cys Glu Gln Cys Gly Lys Cys Lys Cys Gly Glu Cys Thr Ala Pro Arg
 1               5                  10                  15

Thr Leu Pro Ser Cys Leu Ala Cys Asn Arg Gln Cys Leu Cys Ser Ala
            20                  25                  30

Glu Ser Met Val Glu Tyr Gly Thr Cys Met Cys Leu Val Lys Gly Ile
        35                  40                  45

Phe Tyr His Cys Ser Asn Asp Asp Glu Gly Asp Ser Tyr Ser Asp Asn
    50                  55                  60
```

```
Pro Cys Ser Cys Ser Gln Ser His Cys Cys Ser Arg Tyr Leu Cys Met
 65                  70                  75                  80

Gly Ala Met Ser Leu Phe Leu Pro Cys Leu Leu Cys Tyr Pro Pro Ala
                 85                  90                  95

Lys Gly Cys Leu Lys Leu Cys Arg Arg Cys Tyr Asp Trp Ile His Arg
            100                 105                 110

Pro Gly Cys Arg Cys Lys Asn Ser Asn Thr Val Tyr Cys Lys Leu Glu
        115                 120                 125

Ser Cys Pro Ser Arg Gly Gln Gly Lys Pro Ser
    130                 135
```

<210> SEQ ID NO 5
<211> LENGTH: 300
<212> TYPE: PRT
<213> ORGANISM: Mus musculus

<400> SEQUENCE: 5

```
Met Glu Pro Pro Val Pro Gln Ser Ser Val Pro Val Asn Pro Ser Ser
  1               5                  10                  15

Val Met Val Gln Pro Leu Leu Asp Ser Arg Ala Pro His Ser Arg Leu
                 20                  25                  30

Gln His Pro Leu Thr Ile Leu Pro Ile Asp Gln Met Lys Thr Ser His
             35                  40                  45

Val Glu Asn Asp Tyr Ile Asp Asn Pro Ser Leu Ala Pro Ala Thr Gly
 50                  55                  60

Pro Lys Arg Pro Arg Gly Gly Pro Pro Glu Leu Ala Pro Thr Pro Ala
 65                  70                  75                  80

Arg Cys Asp Gln Asp Ile Thr His His Trp Ile Ser Phe Ser Gly Arg
                 85                  90                  95

Pro Ser Ser Val Ser Ser Ser Ser Thr Ser Ser Asp Gln Arg Leu
            100                 105                 110

Leu Asp His Met Ala Pro Pro Val Ala Glu Gln Ala Ser Pro Arg
        115                 120                 125

Ala Val Arg Leu Gln Pro Lys Val His Cys Lys Pro Leu Asp Leu
130                 135                 140

Lys Gly Pro Thr Ala Pro Pro Glu Leu Asp Lys His Phe Leu Leu Cys
145                 150                 155                 160

Glu Ala Cys Gly Lys Cys Lys Cys Lys Glu Cys Ala Ser Pro Arg Thr
                165                 170                 175

Leu Pro Ser Cys Trp Val Cys Asn Gln Glu Cys Leu Cys Ser Ala Gln
            180                 185                 190

Thr Leu Val Asn Tyr Gly Thr Cys Met Cys Leu Val Gln Gly Ile Phe
        195                 200                 205

Tyr His Cys Thr Asn Glu Asp Asp Glu Gly Ser Cys Ala Asp His Pro
    210                 215                 220

Cys Ser Cys Ser Gly Ser Asn Cys Cys Ala Arg Trp Ser Phe Met Gly
225                 230                 235                 240

Ala Leu Ser Val Val Leu Pro Cys Leu Leu Cys Tyr Leu Pro Ala Thr
                245                 250                 255

Gly Cys Val Lys Leu Ala Gln Arg Gly Tyr Asp Arg Leu Arg Arg Pro
            260                 265                 270

Gly Cys Arg Cys Lys His Thr Asn Ser Val Ile Cys Lys Ala Ala Ser
        275                 280                 285

Gly Asp Thr Lys Thr Ser Arg Ser Asp Lys Pro Phe
    290                 295                 300
```

290             295             300

<210> SEQ ID NO 6
<211> LENGTH: 315
<212> TYPE: PRT
<213> ORGANISM: Mus musculus

<400> SEQUENCE: 6

Met Glu Ala Arg Ala Gln Ser Gly Asn Gly Ser Gln Pro Leu Leu Gln
 1               5                  10                  15

Thr Ala His Asp Ser Gly Arg Gln Arg Gly Glu Pro Asp Pro Arg Asp
             20                  25                  30

Ala Leu Thr Gln Gln Val His Val Leu Ser Leu Asp Gln Ile Arg Ala
         35                  40                  45

Ile Arg Asn Thr Asn Glu Tyr Thr Glu Gly Pro Thr Val Val Pro Arg
     50                  55                  60

Pro Gly Leu Lys Pro Ala Pro Arg Pro Ser Thr Gln His Lys His Glu
 65                  70                  75                  80

Arg Leu His Gly Leu Pro Glu His Arg Gln Pro Pro Arg Leu Gln Pro
                 85                  90                  95

Ser Gln Val His Ser Ser Arg Ala Pro Leu Ser Arg Ser Ile Ser Thr
            100                 105                 110

Val Ser Ser Gly Ser Arg Ser Ser Thr Arg Thr Ser Thr Ser Ser Ser
        115                 120                 125

Ser Ser Glu Gln Arg Leu Leu Gly Pro Ser Phe Ser His Gly Pro Ala
    130                 135                 140

Ala Ala Asp Gly Ile Ile Arg Val Gln Pro Lys Ser Glu Leu Lys Pro
145                 150                 155                 160

Gly Asp Ile Lys Pro Leu Ser Lys Asp Leu Gly Leu His Ala Tyr
                165                 170                 175

Arg Cys Glu Asp Cys Gly Lys Cys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255

Gly Val Met Ser Leu Phe Leu Pro Cys Leu Trp Cys Tyr Leu Pro Ala
            260                 265                 270

Lys Gly Cys Leu Lys Leu Cys Gln Gly Cys Tyr Asp Arg Val Asn Arg
        275                 280                 285

Pro Gly Cys Arg Cys Lys Asn Ser Asn Thr Val Cys Cys Lys Val Pro
    290                 295                 300

Thr Val Pro Pro Arg Asn Phe Glu Lys Pro Thr
305                 310                 315

<210> SEQ ID NO 7
<211> LENGTH: 100
<212> TYPE: PRT
<213> ORGANISM: Homo sapiens

<400> SEQUENCE: 7

Pro Leu Pro Leu Asp Gln Arg Leu Leu Ala Ser Ile Thr Pro Ser Pro

```
            1               5               10              15
Ser Gly Gln Ser Ile Ile Arg Thr Gln Pro Gly Ala Gly Val His Pro
                    20              25              30

Lys Ala Asp Gly Ala Leu Lys Gly Glu Ala Glu Gln Ser Ala Gly His
            35              40              45

Pro Ser Glu His Leu Phe Ile Cys Glu Cys Gly Arg Cys Lys Cys
    50              55              60

Val Pro Cys Thr Ala Ala Arg Pro Leu Pro Ser Cys Trp Leu Cys Asn
65              70              75              80

Gln Arg Cys Leu Cys Ser Ala Glu Ser Leu Leu Asp Tyr Gly Thr Cys
                85              90              95

Leu Cys Cys Val
            100

<210> SEQ ID NO 8
<211> LENGTH: 24
<212> TYPE: DNA
<213> ORGANISM: Homo sapiens
<220> FEATURE:
<223> OTHER INFORMATION: Description of Artificial Sequence: primer

<400> SEQUENCE: 8
aggcacccca ggctttacac ttta                                       24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
ttcccgggtc gacgatttcg t                                          21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 10
ccatcctaat acgactcact atagggc                                    27

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 11
actcactata gggctcgagc ggc                                        23

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 12
gtccgggggg atgcacactc cttgcattt                                  29
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13
tggaccacct tgggctggat                                              20
```

US 6,485,920 B1

GROWTH FACTOR ANTAGONIST MATERIALS AND METHODS

The present application is a divisional of U.S. application Ser. No. 09/370,398 filed Aug. 6, 1999 issued as U.S. Pat. No. 6,423,682.

FIELD OF THE INVENTION

The present invention relates to a novel polynucleotide encoding a protein called FGFAn-Hy, which is structurally related to a growth factor antagonist protein, Sprouty, along with therapeutic, diagnostic and research utilities for these and related products.

BACKGROUND

Growth factors, such as fibroblast growth factor (FGF), are ligands for receptor tyrosine kinases (RTK) and are involved in stimulating cellular proliferation and migration. As a result, growth factor and RTK antagonists may be involved in conditions involving uncontrolled growth and vascularization.

Sprouty was initially identified as an antagonist of FGF signaling in the developmental pathway of Drosophila tracheal branching morphogenesis. An FGF family member, Branchless, is the critical determinant of tracheal branching pattern through inducing cell migration which results in branching morphogenesis. It was determined that Branchless induces expression of a potent negative signal, Sprouty, that inhibits branching morphogenesis and was found to act as an negative regulator of tracheal development. Loss of function mutations in the Sprouty gene led to increased tracheal branching while gain of function mutations severely blocked tracheal development. Overexpression of Branchless overrode the Sprouty loss of function mutation indicating that Sprouty's antagonist activity was specific for the FGF activity in this developmental pathway (Hacohen et al. (1998), Cell, 92: 253–263; Metzger et al. (1999), Science, 284:1635–25 1639).

Currently, there are three known human homologs of the Drosophila Sprouty protein denoted human Sprouty-1, Sprouty-2 and Sprouty-3 (genes denoted h-Spry1, h-Spry2, h-Spry3). H-Spry-2 encodes an approximately 35 Kd protein which contains a cysteine-rich domain. This domain is highly conserved among the human homologs (Hacohen et al. (1998), Cell, 92: 253–263).

The Sprouty mouse homolog (sprouty-2, encoded by gene mSpry-2) also was found to regulate bronchial branching patterns in the developing lung. In this system, mSpry-2 inhibited FGF10-induced bronchial branching. The mSpry-2 amino acid sequence is 97% homologous to h-Spry2, indicating that this protein may be highly conserved among different species (Tefft et al. (1999), Curr Biol, 9: 219–222). Another mouse homolog, sprouty-4, has also been identified (De Maximy et al (1999), Mech. Dev. 81, 213–216).

Other evidence indicates that Sprouty may act as a general inhibitor of RTK activity. In addition to its inhibitory effects on FGF signaling, Sprouty expression was shown to antagonize epidermal growth factor (EGF) action in the developing Drosophila eye imaginal disc, larval peripheral nervous system, embryonic central nervous system, developing wing and developing ovary (Casci et al. (1999), Cell, 96: 655–665, Kramer et al. (1999), Development, 126: 2515–2525). Sprouty also inhibits the action of an unrelated RTK, Torso, which initiates the development of terminal structures in the developing Drosophila embryo (Casci et al. (1999), Cell, 96: 655–665).

Sprouty is an intracellular protein which associates with the plasma membrane through its cysteine-rich domain. Sprouty acts within the mitogen activated protein (MAP) kinase signaling cascade, and its inhibitory action has been mapped to be downsteam of the RTK and upstream of ras. This suggests that Sprouty may be binding to adaptor proteins, such as Drk (the Drosophila homolog of Grb2) and Gap1, within the MAP kinase signaling cascade (Casci et al. (1999), Cell, 96: 655–665).

The autonomous manner in which Sprouty works in the eye is different from the non-autonomous manner in which it acts in the tracheal system. It has been speculated that Sprouty may not only act intracellularly to repress signal transduction but may also act on a second signaling relay to repress cell fate in the neighbors of Sprouty-expressing cells (Placzek et al. (1999), Current Biol., 9:R506–510).

Many growth factors, such as FGF, EGF, platelet-derived growth factor and insulin-like growth factor, elicit their response through RTKs. Activation of the RTK initiates signaling through the MAP kinase cascade. As a result, the MAP kinase signaling pathway is involved in many cellular actions including proliferation, migration, angiogenesis, and organogenesis.

Thus, there is a need for growth factor and MAP kinase signaling antagonists, such as Sprouty family members, which may be useful in modulating cell growth, migration and vascularization.

SUMMARY OF THE INVENTION

The compositions of the present invention include novel isolated polypeptides, in particular, novel human growth factor antagonist proteins and active variants thereof, isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies.

The compositions of the present invention additionally include vectors, including expression vectors, containing the polynucleotides of the invention, cells genetically engineered to contain such polynucleotides and cells genetically engineered to express such polynucleotides.

A nucleotide sequence encoding a growth factor antagonist protein designated FGFAn-Hy is set forth in SEQ ID NO: 1, and its deduced amino acid sequence is set forth in SEQ ID NO: 2. This growth factor antagonist protein is believed to play a role in the mitogen activated protein (MAP) kinase signaling pathway involving receptor tyrosine kinases (RTKs) and ras. The polypeptide set out in SEQ ID NO: 2 is 300 amino acids in length, and appears to have no readily identifiable signal sequence, indicating that it is most likely an intracellular protein like the Drosophila growth factor antagonist protein Sprouty. The polypeptide of SEQ ID NO: 2 displays amino acid homology with the Drosophila Sprouty, as well as with mammalian family members human Sprouty-1, -2 and -3 and mouse Sprouty-2 and 4. An alignment of FGFAn-Hy and other members of the sprouty family is shown in FIG. 1. FGFAn-Hy is most closely related to mouse sprouty-4 (92% amino acid sequence identity). Additional family members can be identified using SEQ ID NO: 1 as a molecular probe.

The polynucleotides of the invention include naturally occurring or wholly or partially synthetic DNA, e.g., cDNA and genomic DNA, and RNA, e.g., mRNA. The isolated polynucleotides of the invention include, but are not limited to, a polynucleotide encoding a polypeptide comprising the amino acid sequence of SEQ ID NO: 2 or a portion thereof corresponding to the full length or mature protein. The isolated polynucleotides of the invention further include, but are not limited to, a polynucleotide comprising the nucleotide sequence of SEQ ID NO: 1; a polynucleotide comprising the fill length protein coding sequence of SEQ ID NO: 1; and a polynucleotide comprising the nucleotide sequence of the mature protein coding sequence of SEQ ID NO: 1. The polynucleotides of the present invention also include, but are not limited to, polynucleotides that encode polypeptides with growth factor antagonist activity and that hybridize under stringent hybridization conditions to the complement of (a) the nucleotide sequence of SEQ ID NO: 1, or (b) a nucleotide sequence encoding the amino acid sequence of SEQ ID NO: 2; a polynucleotide which is an allelic variant of any polynucleotide recited above; a polynucleotide which encodes a species homolog of any of the proteins recited above; or a polynucleotide that encodes a polypeptide comprising a specific domain or truncation of the polypeptide having an amino acid sequence of SEQ ID NO: 2. The polynucleotides of the invention additionally include the complement of any of the polynucleotides recited above.

The isolated polypeptides of the invention include, but are not limited to, a polypeptide comprising the amino acid sequence of SEQ ID NO: 2 or a portion thereof corresponding to the full length or mature protein. Polypeptides of the invention also include polypeptides with growth factor antagonist activity that are encoded by (a) polynucleotides set out in SEQ ID NO: 1; or (b) polynucleotides that hybridize to the complement of the polynucleotides of (a) under stringent hybridization conditions. Biologically or immunologically active variants of the growth factor antagonist protein sequence of SEQ ID NO: 2 and "substantial equivalents" thereof (e.g., with 65%, 70%, 75%, 80%, 85%, 90%, 95%, 98% or 99% amino acid sequence identity) that retain growth factor antagonist activity are also contemplated. The polypeptides of the invention may be wholly or partially chemically synthesized but are preferably produced by recombinant means using the genetically engineered cells (e.g. host cells) of the invention.

Protein compositions of the present invention may further comprise an acceptable carrier, such as a hydrophilic, e.g., pharmaceutically acceptable, carrier.

The invention also relates to methods for producing polypeptides of the invention comprising growing a culture of the cells of the invention in a suitable culture medium under conditions permitting expression of the desired polypeptide, and purifying the protein from the cells or the culture medium in which the cells are grown. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect or quantify the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantitating the polypeptide in tissue. The polypeptides of the invention can also be used as molecular weight markers, and as a food supplement.

Methods are also provided for preventing, treating, or ameliorating a medical condition which comprises the step of administering to a mammalian subject a therapeutically effective amount of a composition comprising a protein of the present invention and a pharmaceutically acceptable carrier.

Where the polypeptide has growth factor antagonist or MAP kinase signaling antagonist activity, the polypeptides and polynucleotides of the invention can be utilized, for example, as part of methods for the prevention and/or treatment of disorders involving cell growth and proliferation, such as angiogenesis, or any of the disorders described below. Where the polypeptide promotes cell growth and proliferation, polypeptides and polynucleotides can be utilized to promote tissue growth, for example, as as part of treatment for increasing vascularization, wound healing, or any of the other disorders described herein.

The methods of the present invention further relate to methods for detecting the presence of the polynucleotides or polypeptides of the invention in a sample. Such methods can, for example, be utilized as part of prognostic and diagnostic evaluation of disorders as recited herein and for the identification of subjects exhibiting a predisposition to such conditions. The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited herein.

Mutations in the FGFAn-Hy gene may be associated with uncontrolled cellular proliferation, such as cancer, and the identification of such mutations and detection of these mutations in subjects may provide important diagnostic and prognostic information.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited herein. Such methods can include, but are not limited to, assays for identifying compounds and other substances that interact with (e.g., bind to) the polypeptides of the invention.

The methods of the invention also include methods for the treatment of disorders as recited above which may involve the administration of such compounds to individuals exhibiting symptoms or tendencies related to disorders as recited herein. In addition, the invention encompasses methods for treating diseases or disorders as recited herein comprising the step of administering compounds and other substances that modulate the overall activity of the target gene products. Compounds and other substances can effect such modulation either on the level of target gene expression or target protein activity.

BRIEF DESCRIPTION OF THE DRAWINGS

FIGS. 1A–C shows an alignment of FGFAn-Hy amino acid sequence (also called CG165 and set forth in SEQ ID NO: 2) with: human sprouty-2 (SEQ ID NO: 3), human sprouty-1 (Genbank Accession No. AAC39566, set forth in SEQ ID NO: 4), mouse sprouty-4 (SEQ ID NO: 5), mouse sprouty-2 (SEQ ID NO: 6), and human sprouty-3 (Genbank Accession No. AAC39567, set forth in SEQ ID NO: 7). The alignment was generated using the Clustal Method with PAM250 residue weight table. Amino acid numbers for each sequence are labelled accordingly. Gaps are presented as dashes, and shaded residues match the consensus exactly.

DETAILED DESCRIPTION OF THE INVENTION

1. DEFINITIONS

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The term "stringent" is used to refer to conditions that are commonly understood in the art as stringent. Stringent conditions can include highly stringent conditions (e.g., hybridization to filter-bound DNA under in 0.5 M $NaBPO_4$, 7% sodium dodecyl sulfate (SDS), 1 mM EDTA at 65° C., and washing in 0.1×SSC/0.1% SDS at 68° C.), and moderately stringent conditions (e.g., washing in 0.2×SSC/0.1% SDS at 42° C.). Other exemplary hybridization conditions are described herein in the examples.

In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biologic and/or immunologic activities of any naturally occurring polypeptide. According to the invention, the term "biologically active" with reference to the growth factor antagonist polypeptides of the invention means that the polypeptide retains at least one of the biological activities of FGFAn-Hy, preferably the growth factor antagonist activity, while the term "immunologically active" with reference to the growth factor antagonist polypeptides of the invention means that the polypeptide retains at least one of the immunologic or antigenic activities of FGFAn-Hy.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, for example, recombinant DNA techniques. Guidance in determining which amino acid residues may be replaced, added or deleted without abolishing activities of interest, such as growth factor antagonist activity, may be found by comparing the sequence of the particular polypeptide with that of homologous human or other mammalian growth factor antagonist polypeptides and minimizing the number of amino acid sequence changes made in regions of high homology (conserved regions) or by replacing amino acids with consensus sequence.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.2 or less). Such a sequence is said to have 80% sequence identity to the listed sequence. In one embodiment, a substantially equivalent, e.g., mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity). Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method.

Nucleic acid sequences encoding such substantially equivalent sequences, e.g., sequences of the recited percent identities, can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2): 134–143) and factors released from damaged cells (e.g. Interleukin-1 Receptor Antagonist, see Arend, W. P. et. al. (1998) Annu. Rev. Immunol. 16:27–55)

Each of the above terms is meant to encompasses all that is described for each, unless the context dictates otherwise.

NUCLEIC ACIDS AND POLYPEPTIDES OF THE INVENTION

Nucleotide and amino acid sequences of the invention are reported below. Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (for example, without a signal sequence or precursor sequence) of the disclosed proteins. The full-length form of the such proteins is identified in the sequence listing by translation of the nucleotide sequence of each disclosed clone. The mature form of such protein may be obtained by expression of the disclosed full-length polynucleotide in a suitable mammalian cell or other host cell. The sequence of the mature form of the protein is also determinable from the amino acid sequence of the full-length form. Where protein of the present invention is membrane bound, soluble forms of the protein are also provided. In such forms part or all of the regions causing the protein to be membrane bound are deleted so that the protein is fully secreted from the cell in which it is expressed.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Species homologs of the disclosed polynucleotides and proteins are also provided by the present invention. Species homologs may be isolated and identified by making suitable probes or primers from the sequences provided herein and screening a suitable nucleic acid source from the desired species. The invention also encompasses allelic variants of the disclosed polynucleotides or proteins; that is, naturally-occurring alternative forms of the isolated polynucleotide which also encode proteins which are identical, homologous or related to that encoded by the polynucleotides. The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides. Species homologs of the disclosed polynucleotides and proteins are also provided by the present invention. Species homologs may be isolated and identified by making suitable probes or primers from the sequences provided herein and screening a suitable nucleic acid source from the desired species. The invention also encompasses allelic variants of the disclosed polynucleotides or proteins; that is, naturally-occurring alternative forms of the isolated polynucleotide which also encode proteins which are identical, homologous or related to that encoded by the polynucleotides.

2. NUCLEIC ACIDS OF THE INVENTION

The isolated polynucleotides of the invention include, but are not limited to, a polynucleotide encoding a polypeptide comprising the amino acid sequence of SEQ ID NO: 2 or the mature protein portion thereof A preferred nucleic acid sequence is set forth in SEQ ID NO: 1.

The isolated polynucleotides of the invention further include, but are not limited to a polynucleotide comprising the nucleotide sequence of SEQ ID NO: 1; a polynucleotide comprising the full length protein coding sequence of SEQ ID NO: 1; and a polynucleotide comprising the nucleotide sequence of the mature protein coding sequence of SEQ ID NO: 1. The polynucleotides of the present invention also include, but are not limited to, polynucleotides that encode polypeptides with growth factor antagonist activity and that hybridize under stringent hybridization conditions to the complement of either (a) the nucleotide sequence of SEQ ID NO: 1 or (b) a nucleotide sequence encoding the amino acid sequence of SEQ ID NO: 2; a polynucleotide which is an allelic variant of any polynucleotide recited above; a polynucleotide which encodes a species homolog of any of the proteins recited above; or a polynucleotide that encodes a polypeptide comprising a specific domain or truncation of the polypeptide of SEQ ID NO: 2.

The polynucleotides of the invention additionally include the complement of any of the polynucleotides recited above.

The polynucleotides of the invention also provide polynucleotides including nucleotide sequences that are substantially equivalent to the polynucleotides recited above. Polynucleotides according to the invention can have at least about 65%, more typically at least about 70%, at least about 75%, at least about 80%, at least about 85% or at least about 90%, and even more typically at least about 95%, sequence identity to a polynucleotide recited above. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NO: 1, or a representative fragment thereof, or a nucleotide sequence at least 99.9% identical to SEQ ID NO: 1 with a sequence from another isolate of the same species.

To accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NO: 1 or a fragment thereof or any other polynucleotides of the invention. In one embodiment, the recombinant constructs of the present invention comprise a vector, such as a plasmid or viral vector, into which a nucleic acid having the sequence of SEQ ID NO: 1 or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., Nucleic Acids Res. 19, 44854490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequence of SEQ ID NO: 1, which fragment is greater than about 10 bp, preferably 20–50 bp, greater than 100 bp, greater than 300 bp, or greater than 500 bp. In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells, and sequences such as FLAG or poly-histidine sequences useful for purifying the expressed protein.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

3. HOSTS

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

Knowledge of growth factor antagonist DNA sequences allows for modification of cells to permit, or increase, expression of endogenous growth factor antagonists. Cells can be modified (e.g., by homologous recombination) to provide increased growth factor antagonist expression by replacing, in whole or in part, the naturally occurring promoter with all or part of a heterologous promoter so that the cells express growth factor antagonist protein at higher levels. The heterologous promoter is inserted in such a manner that it is operatively linked to growth factor antagonist encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the growth factor antagonist coding sequence, amplification of the marker DNA by standard selection methods results in co-amplification of the growth factor antagonist coding sequences in the cells.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coil* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast, insects or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

Exemplary gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4. POLYPEPTIDES OF THE INVENTION

The isolated polypeptides of the invention include, but are not limited to, a polypeptide comprising the amino acid sequence of SEQ ID NO: 2 or the amino acid sequence encoded by the DNA of SEQ ID NO: 1 or a portion thereof corresponding to the full length or mature protein. Polypeptides of the invention also include polypeptides with growth factor antagonist activity that are encoded by (a) the polynucleotide of SEQ ID NO: 1, or (b) polynucleotides encoding SEQ ID NO: 2 or (b) polynucleotides that hybridize to the complement of the polynucleotides of either (a) or (b) under stringent hybridization conditions. Biologically active or immunologically active variants of the growth factor antagonist protein sequence of SEQ ID NO: 2 and "substantial equivalents" thereof (e.g., with 65%, 70%, 75%, 80%, 85%, 90%, typically 95%, more typically 98% or most typically 99% amino acid identity) that retain biological activity, preferably growth factor antagonist activity, are also contemplated. Polypeptides encoded by allelic variants may have a similar or increased or decreased activity compared to the polypeptides of SEQ ID NO: 2.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the cells or the culture medium, and further purified. Preferred embodiments include those in which the protein produced by such process is a full length or mature form of the protein.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from host cells which produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology. Polypeptide fragments that retain biological/immunological activity include fragments encoding greater than about 100 amino acids, or greater than about 200 amino acids, and fragments that encode specific protein domains.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are collections of microorganisms (including bacteria and fungi), animals, plants or other vegetation, or marine organisms, and libraries of mixtures for screening may be created by: (I) fermentation and extraction of broths from soil, plant or marine microorganisms or (2) extraction of the organisms themselves. Natural product libraries include polyketides, non-ribosomal peptides, and variants (non-naturally occurring) variants thereof For a review, see *Science* 282:63–68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997). For reviews and examples of peptidomimetic libraries, see Al-Obeidi et al., *Mol. Biotechnol*, 9(3):205–23 (1998); Hruby et al., *Curr Opin Chem Biol*, 1(1):114–19 (1997) Dorner et al., *Bioorg Med Chem*, 4(5):709–15 (1996) (alkylated dipeptides).

Identification of modulators through use of the various libraries described herein permits modification of the candidate "hit" (or "lead") to optimize the capacity of the "hit" to bind a polypeptide of the invention. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells such as radioisotopes. The toxin-binding molecule complex is then targeted to a tumor or other cell by the specificity of the binding molecule for a polypeptide of the invention. Alternatively, the polypeptide of the invention or binding molecules may be complexed with imaging agents for targeting and imaging, e.g., areas of vascularization.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MAXBAT™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, HEPARIN-TOYOPEARL™ or CIBACROM BLUE 3GA SEPHAROSE™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include FGFAn-Hy analogs or variants. This embraces fragments of FGFAn-Hy, as well as analogs (variants) thereof in which one or more amino acids has been deleted, inserted, or substituted. Analogs of the invention also embrace fusions or modifications of FGFAn-Hy wherein the protein or analog is fused to another moiety or moieties, e.g., targeting moiety or another therapeutic agent. Such analogs may exhibit improved properties such as activity and/or stability. Examples of moieties which may be fused to FGFAn-Hy or an analog include, for example, targeting moieties which provide for the delivery of polypeptide to desired cell types. Other moieties which may be fused to FGFAn-Hy or an analog include therapeutic agents which are used for treatment of indications as described herein.

5. GENE THERAPY

Mutations in the FGFAn-Hy gene may result in loss of normal function of the encoded protein. The invention thus provides gene therapy to restore normal FGFAn-Hy activity or to treat disease states involving FGFAn-Hy (for example, various forms of cancer described herein). Delivery of a functional FGFAn-Hy gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25–20 (1998). For additional reviews of gene therapy technology see Friedmann, Science, 244: 1275–1281 (1989); Verma, Scientific American: 68–84 (1990); and Miller, Nature, 357: 455–460 (1992). Alternatively, it is contemplated that in other human disease states, preventing the expression of or inhibiting the activity of FGFAn-Hy will be useful in treating the disease states. It is contemplated that antisense therapy or gene therapy could be applied to negatively regulate the expression of FGFAn-Hy.

5.1 TRANSGENIC ANIMALS

In methods to determine biological functions of FGFAn-Hy in vivo, one or more growth factor antagonist genes are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the role(s) FGFAn-Hy play in biological processes, and preferably in disease states. Transgenic animals are useful as model systems to identify compounds that modulate growth factor activity. Transgenic animals, preferably non-human mammals, are produced using methods as described in U.S. Pat. No 5,489,743 and PCT Publication No. WO94/28122, incorporated herein by reference.

Transgenic animals can be prepared wherein all or part of an FGFAn-Hy promoter is either activated or inactivated to alter the level of expression of the FGFAn-Hy protein. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

6. USES AND BIOLOGICAL ACTIVITY

The biological activity of a polypeptide of the invention may manifest as, e.g., growth factor antagonist or growth promoting activity. The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA). The mechanism underlying the particular condition or pathology will dictate whether FGFAn-Hy polypeptides, binding partners thereof, or modulators (enhancers and inhibitors thereof) would be beneficial to the subject in need of treatment.

The growth factor antagonist protein FGFAn-Hy is believed to play a role in the response of cells to growth factors, particularly through the mitogen activated protein (MAP) kinase signaling pathway involving receptor tyrosine kinases (RTKs) and ras. Growth factors and the MAP kinase signaling pathway are involved in many cellular actions including proliferation, migration, angiogenesis, and organogenesis. Thus, growth factor antagonists or MAP kinase signaling inhibitors are expected to inhibit angiogenesis and cell proliferation and migration, while growth factor agonists or MAP kinase signaling enhancers are expected to promote these activities. It is contemplated that multiple different growth factor antagonists may be administered to reduce cellular proliferation, migration or growth; similarly, it is contemplated that multiple different growth factor agonists (e.g., growth factors together with small molecule inhibitors of growth factor antagonists) may be administered to promote cellular proliferation, migration or growth.

Angiogenesis plays a role in chronic inflammation, including chronic pancreatitis, dermatosis associated with chronic inflammation, including psoriasis, cirrhosis, asthma, multiple sclerosis, arthritis, including rheumatoid arthritis, reactive arthritis and chronic inflammatory arthritis, autoimmune disorders, including vasculitis, glomerulonephritis, experimental allergic encephalomyelitis (EAE), lupus, myasthenia gravis, ulcerative colitis, Crohn's disease, inflammatory bowel disease, chronic inflammation associated with hemodialysis, granulocyte transfusion associated syndrome; rejection reactions after allograft and xenograft transplantation, including graft versus host disease; and other chronic inflammatory disorders, including those associated with autoimmune diseases Angiogenesis in the eye is involved in ocular neovascularization, proliferative retinopathy, macular degeneration, and diabetic ocular disease, in particular, diabetic iris neovascularization and retinopathy.

Coronary atheroma are highly vascularized by a fragile capillary network, and rupture of these newly formed capillaries when they are exposed to high intravascular pressures may lead to hemorrhage into atherosclerotic plaques and vessel occlusion. Inhibition of angiogenesis thus may reduce the growth of atherosclerotic plaques and may be useful in the treatment of atherosclerosis, ischemic heart disease, myocardial infarction, coronary heart disease, restenosis, particularly following balloon angiography, neointimal hyperplasia, disruption of intercellular junctions in vascular endothelium, hypertension, vessel injury, arterial ischemia, arterial stenosis, peripheral vascular disease, stroke, coronary obstruction, and periventricular leukomalacia, chronic corpulmonalea (disease of the right or both ventricle(s) of the heart), and other conditions associated with decreased or increased myocardial revascularization. Agents that modulate angiogenesis are also expected to be useful in vascular remodeling as an alternative to coronary artery bypass surgery to prevent myocardial infarction.

Introduction of angiogenic factors into ischemic myocardium is expected to enhance the development of collateral vessels, accelerate healing of necrotic tissue, and prevent infarct expansion and cardiac dilation. Similarly, essential hypertension is based on an impaired capacity for vascular growth.

Methods of the invention also include treatment for cardiovascular conditions and pathologies including modified microvascular hyperpermeability, hemostasis, microvascular disease associated with impaired angiogenesis, pulmonary vascular disorders in portal hypertension, and capillary leak syndrome. Angiogenesis modulators are also expected to be useful in enhancing the strength and integrity of vessels, possibly decreasing the likelihood of vessel rupture and associated artery blockage at sites of atherosclerotic plaques.

Angiogenesis is also important in bone conditions including osteoporosis, osteoradionecrosis, osteonecrosis generally, osteonecrosis of the femoral head, fracture healing and repair generally, fracture healing associated with autogenous and allogeneic bone grafts, and necrosis and hypoxia of bone adjacent a fracture.

Angiogenesis also occurs during the female reproductive cycle and is involved in endometriosis, uterine fibroids, other conditions associated with dysfunctional vascular proliferation (including endometrial microvascular growth) during the female reproductive cycle.

Angiogenesis is also involved in abnormal vascular growth, including cerebral arteriovenous malformations (AVMs), varicose veins, gastrointestinal mucosal injury and repair, ulceration of the gastroduodenal mucosa in patients with a history of peptic ulcer disease, ischemic tissue resulting from stroke, a wide spectrum of pulmonary vascular disorders in liver disease and portal hypertension in patients with nonhepatic portal hypertension, including hepatopulmonary syndrome and pulmonary hypertension (portopulmonary hypertension), hemangiopericytoma, pyogenic granuloma, and liver failure.

Angiogenesis is also of considerable importance in cancer conditions because new vessel production is required to support the rapid growth of cancer cells. Inhibition of angiogenesis thus may promote tumor regression in adult and pediatric oncology, including reducing growth of solid tumors/malignancies, locally advanced tumors, metastatic cancer, human soft tissue sarcomas, cancer metastases, including lymphatic metastases, blood cell malignancies, including multiple myeloma, leukemias, effusion lymphomas (body cavity based lymphomas), lung cancer, including small cell carcinoma, non-small cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, prostate cancer, malignancies of the female genital tract, including ovarian carcinoma, uterine endometrial cancers, and solid tumors in the ovarian follicle, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas, skin cancers, including malignant melanoma, tumor progression of human skin keratinocytes, and squamous cell cancer, hemangiopericytoma, and Kaposi's sarcoma.

Additional uses for polypeptides of the present invention, as well as modulators there of, are described below.

Modulation of cell proliferation and migration can be useful in many pathological conditions, including pre-eclampsia decidua, neurodegeneration, abnormal embryonic development, abnormal wound healing, conditions associated with neoplastic growth, large-bowel diseases generally and specifically ulcerative colitis, small axillary node-negative breast carcinomas and distant metastasis, colorectal carcinomas, inflammation in general, chronic and seasonal asthma, abnormal osteoblastic differentiation, tendon disease including abnormal tendon formation and degenerate tendons, abnormal collagen fibril organization, mononuclear cell infiltration, angiopoiesis, chondrogenic tumors, proliferative activity of tumor cells in enchondromas and chondrosarcomas, alterations of extracellular matrix, tumor development, active scar formation, granulomas in sarcoidosis, cryptic fibrosing alveolitis (CFA), abnormal assembly and activity of focal adhesions, neointima formation after acute vascular injury, new growth and expansion within primary atherosclerotic plaques, and intimal repair and luminal narrowing in restenosis after angioplasty.

Use of growth factor antagonist proteins also is implicated in treatment methods to reduce epithelial and endothelial proliferation or differentiation, to improve skin texture, to reduce scarring, to improve wound healing, and in other conditions associated with tissue growth as described below.

6.1. RESEARCH USES AND UTILITIES

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

6.2. NUTRITIONAL USES

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

6.3. CYTOKINE AND CELL PROLIFERATION/ DIFFERENTIATION ACTIVITY

A protein of the present invention may exhibit cytokine, cell proliferation (either inducing or inhibiting) or cell differentiation (either inducing or inhibiting) activity or may induce production of other cytokines in certain cell populations.

6.4. IMMUNE STIMULATING OR SUPPRESSING ACTIVITY

A protein of the present invention may also exhibit immune stimulating or immune suppressing activity, including without limitation the activities for which assays are described herein. For example, polypeptides of the invention may be used to modulate the immune response in the treatment of leukopaenia, immune coagulation, inflammatory reactions and autoimmune disease.

6.5. HEMATOPOIESIS REGULATING ACTIVITY

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis.

6.6. TISSUE GROWTH ACTIVITY

A protein of the present invention, particularly proteins that promote angiogenesis or vascularization, also may have utility in compositions used for bone, cartilage, tendon, ligament and/or nerve tissue growth or regeneration, as well as for wound healing and tissue repair and replacement, and in the treatment of burns, incisions and ulcers, and in treatment of conditions involving hypovascularization.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome.

Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of wounds, including without limitation pressure ulcers, ulcers associated with vascular insufficiency, , gastric ulcers, surgical and traumatic wounds, burns and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

6.7. CHEMOTACTIC/CHEMOKINETIC ACTIVITY

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes.

6.8. HEMOSTATIC AND THROMBOLYTIC ACTIVTY

A protein of the invention may also exhibit hemostatic or thrombolytic activity. A polynucleotide of the invention can encode a polypeptide exhibiting such attributes. Such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

6.10. RECEPTOR/LIGAND ACTIVITY

A protein of the present invention may also demonstrate activity as receptors, receptor ligands or inhibitors or agonists of receptor/ligand interactions. A polynucleotide of the invention can encode a polypeptide exhibiting such characteristics.

By way of example, the polypeptides of the invention may be used as a ligand for a receptor thereby modulating (i.e., enhancing or inhibiting) the biological activity of that receptor. Whether the polypeptides of the invention exhibit agonist, partial agonist, antagonist, or partial antagonist activity for a particular receptor, such as a growth factor receptor, in a particular cell type can be determined by conventional techniques known to those skilled in the art. Examples of cells that may be contacted with the protein of the invention include, but are not limited to, mammalian cells such as endothelial cells.

Studies characterizing drugs or proteins as agonist or antagonist or partial agonists a partial antagonist require the use of other proteins as competing ligands. The polypeptides of the present invention are expected to exhibit an affinity for growth factor receptors or proteins in the MAP kinase signaling pathway. The polypeptides of the invention may be labeled by being coupled to radioisotopes, colorimetric molecules or a toxin molecules by conventional methods. ("Guide to Protein Purification" Murray P. Deutscher (ed) Methods in Enzymology Vol. 182 (1990) Academic Press, Inc. San Diego) and used in both in vivo and in vitro to bind to Tie-2. Examples of radioisotopes include, but are not limited to, tritium and carbon-14. Examples of colorimetric molecules include, but are not limited to, fluorescent molecules such as fluorescamine, or rhodamine or other colorimetric molecules. Examples of toxins include, but are not limited, to ricin. By way of example, the proteins coupled to such molecules are useful in studies involving in vivo or in vitro metabolism of growth factor antagonists.

6.11 DRUG SCREENING WITH GROWTH FACTOR ANTAGONIST POLYPEPTIDES

This invention is particularly useful for screening compounds by using the growth factor antagonist polypeptides of the invention, particularly binding fragments, in any of a variety of drug screening techniques. The polypeptides employed in such a test may either be free in solution, affixed to a solid support, borne on a cell surface or located intracellularly. One method of drug screening utilizes eukaryotic or prokaryotic host cells which are stably transformed with recombinant nucleic acids expressing the desired polypeptide. Drugs are screened against such transformed cells in competitive binding assays. Such cells, either in viable or fixed form, can be used for standard binding assays. One may measure, for example, the formation of complexes between polypeptides of the invention and the agent being tested or examine the diminution in complex formation between the growth factor antagonist polypeptides and an appropriate cell line, which are well known in the art.

6.11.1 ASSAY FOR RECEPTOR BINDING ACTIVITY

The invention also provides methods to detect specific binding of an growth factor antagonist polypeptide of the invention to a binding partner polypeptide, and in particular a receptor polypeptide. Receptors expected to be useful in binding assays of this type may be identified using assays well known and routinely practiced in the art.

In one embodiment, receptor antagonist activity of the growth factor antagonist FGFAn-Hy polypeptides of the invention is determined using a method that involve (1) forming a mixture comprising growth factor receptor, and/or its agonists and antagonists (or agonist or antagonist drug candidates) and/or antibodies specific for the FGFAn-Hy polypeptides of the invention; (2) incubating the mixture under conditions whereby, but for the presence of said FGFAn-Hy polypeptide of the invention and/or agonists and antagonists (or agonist or antagonist drug candidates) and/or antibodies specific for the FGFAn-Hy polypeptides of the invention, the FGFAn-Hy binds to the receptor; and (3) detecting the presence or absence of specific binding of FGFAn-Hy to the receptor.

The art provides numerous assays particularly useful for identifying previously unknown binding partners for growth factor antagonist polypeptides of the invention. For example, expression cloning, using mammalian or bacterial cells, can be used to identify polynucleotides encoding binding partners. As another example, affinity chromatography with an immobilized growth factor antagonist polypeptide can be used to isolate polypeptides that recognize and bind a polypeptide of the invention. As still another example, overlay assays can be used to identify binding partner polypeptides.

6.11.2 ASSAY FOR ANTAGONISTS AND AGONISTS OF GROWTH FACTOR ACTIVITY

Numerous techniques are known in the art to assay for agonists and antagonists of growth factor or MAP kinase signaling activity (which include the FGFAn-Hy polypeptides of the invention, antibodies thereto, and modulators of FGFAn-Hy expression or activity, e.g., antisense polynucleotides). For example, interactions of growth factors with agonists or antagonists have been studied in a number of models such as Casci et al. (1999), Cell, 96: 655–665; Kramer et al. (1999), Development, 126: 2515–2525; Tefft et al. (1999), Curr Biol, 9: 219–222; Hacohen et al. (1998), Cell, 92: 253–263; Metzger et al. (1999), Science, 284:1635–1639; Chang et al. (1999), Development 126:3347–3357; Yu et al. (1992), J. Exp. Med. 175:1073–80; Francois et al. (1994), Genes Dev. 8:2602–16; Coice et al. (1996), J. Biol. Chem. 271:13110–15. Any model known in the art is suitable for evaluating the activity of FGFAn-Hy polypeptides of the invention, including variants of FGFAn-Hy.

In other examples, the mouse cornea (micropocket) neovascularization assay [Asahara, et al., Circ. Res 83:233–240 (1998)] permits in vivo analysis of angiogenesis modulating activity. Vessel formation can be measured as described in Koblizek, et al., Curr. Biol. 8:529–532 (1998). As another example, angiogenesis can be assessed using the Matrigel™ model [Passaniti, et al., Lab. Invest. 67:519–528 (1992)]. This model uses a Matrigel™ basement membrane preparation mixed with FGF-2 and heparin, which induces intense neovascularization within the gel when injected subcutaneously into mice. The extent of angiogenesis is quantitated by measuring the hemoglobin content of the gels. Compounds that neutralize the angiogenic properties of heparin will inhibit angiogenesis in the model.

In addition, effects of growth factor agonists or antagonists can be evaluated in an experimental animal model of rheumatoid arthritis. One experimental model system is adjuvant induced arthritis in rats, using a protocol described by J. Holoshitz, et at., 1983, Science, 219:56, or by B. Waksman et al., 1963, Int. Arch. Allergy Appl. Immunol., 23:129. Induction of the disease can be caused by a single injection, generally intradermally, of a suspension of killed *Mycobacterium tuberculosis* in complete Freund's adjuvant (CFA). The route of injection can vary, but rats may be injected at the base of the tail with an adjuvant mixture. The test compound is administered in phosphate buffered solution (PBS) at a dose of about 1–5 mg/kg. The control consists of administering PBS only. The challenge and treatment procedure may be carried out by intradermally injecting killed Mycobacterium tuberculosis in CFA followed by immediately administering the test compound, followed by treatment every day or every other day until day 24. Periodically (e.g., at 14, 15, 18, 20, 22, and 24 days) after injection of Mycobacterium CFA, an overall arthritis score may be obtained as described by J. Holoskitz above. An analysis of the data would reveal that the test compound would have a dramatic effect on the swelling of the joints as measured by a decreased arthritis score.

6.12. ANTI-INFLAMMATORY ACTIVITY

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material. In particular, the polypeptides of this invention may be utilized to prevent or treat condition such as, but not limited to, utilized, for example, as part of methods for the prevention and/or treatment of disorders involving sepsis, acute pancreatitis, endotoxin shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an antiproliferative agent such as for acute or chronic mylegenous leukemia or in the prevention of premature labor secondary to intrauterine infections.

6.13. LEUKEMIAS

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monotypic, erythroleukemia, chronic leukemia, chronic myelocytic (granulocytic) leukemia and chronic lymphocytic leukemia (for a review of such disorders, see Fishman et al., 1985, Medicine, 2d Ed., J.B. Lippincott Co., Philadelphia).

6.14. NERVOUS SYSTEM DISORDERS

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo. Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

6.15. OTHER ACTIVITIES

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

6.16 IDENTIFICATION OF POLYMORPHISMS

The demonstration of polymorphisms, for example the polymorphisms illustrated below, makes possible the identification of such polymorphisms in human subjects and the pharmacogenetic use of this information for diagnosis and treatment. Such polymorphisms may be associated with, e.g., differential predisposition or susceptibility to various disease states (such as disorders involving vascular stability or neovascularization) or a differential response to drug administration, and this genetic information can be used to tailor preventive or therapeutic treatment appropriately. For example, the existence of a polymorphism associated with a predisposition to neovascularization makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labeled nucleotides). In addition, traditional restriction fragment length polymorphism analysis (using restriction enzymes that provide differential digestion of the genomic DNA depending on the presence or absence of the polymorphism) may be performed.

Alternatively a polymorphism resulting in a change in the amino acid sequence could also be detected by detecting a corresponding change in amino acid sequence of the protein, e.g., by an antibody specific to the variant sequence.

7. THERAPEUTIC METHODS

The novel polypeptides (including fragments, analogs and variants and antibodies) of the invention have numerous applications in a variety of therapeutic methods. Examples of therapeutic applications include, but are not limited to, those exemplified below.

7.1 PHARMACEUTICAL FORMULATIONS AND ROUTES OF ADMINISTRATION

A protein of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, growth factors, or other hematopoietic factors such as M-CSF, GM-CSF, TNF, IL-1, IL-2, IL-3, IL4, IL-5, IL-6, IL-7, IL-8, IL-9, IL-10, IL-11, IL-12, L-13, L-14, L-15, IL-16, IL-17, IL-18, IFN, TNF0, TNF1, TNF2, G-CSF, Meg-CSF, GM-CSF, thrombopoietin, stem cell factor, and erythropoietin. Particularly preferred are compositions that include other growth factor antagonists, such as human FGF antagonists (e.g., SEQ ID NOS: 4 and 7), aFGF' [Yu et al. (1992), J. Exp. Med. 175:1073–80], short gastrulation gene orthologs [Francois et al. (1994), Genes Dev. 8:2602–16], hepatocyte growth factor/NK1 [Coice et al. (1996), J. Biol. Chem. 271:13110–15] or factors that modulate angiogenesis, such as angiopoietins Ang-1, Ang-2, Ang-4, Ang-Y, and/or the human angiopoietin-like polypeptide, and/or vascular endothelial growth factor (VEGF). Preferred growth factors for use in pharmaceutical compositions of the invention include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor $\alpha$ cytokine-induced neutrophil chemotactic factor 1, cytokine-induced neutrophil, chemotactic factor $2\alpha$, cytokine-induced neutrophil chemotactic factor $2\beta$, $\beta$ endothelial cell growth factor, endothelin 1, epidermal growth factor, epithelial-derived neutrophil attractant, fibroblast growth factor 4, fibroblast growth factor 5, fibroblast growth factor 6 fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor $\alpha 1$, glial cell line-derived neutrophic factor receptor $\alpha 2$, growth related protein, growth related protein $\alpha$, growth related protein $\beta$, growth related protein $\gamma$, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptor $\beta$, pre-B cell growth stimulating factor, stem cell factor, stem cell factor receptor, transforming growth factor $\alpha$, transforming growth factor $\beta$, transforming growth factor $\beta 1$, transforming growth factor $\beta 1.2$, transforming growth factor $\beta 2$, transforming growth factor $\beta 3$, transforming growth factor $\beta 5$, latent transforming growth factor $\beta 1$, transforming growth factor $\beta$ binding protein I, transforming growth factor $\beta$ binding protein II, transforming growth factor $\beta$ binding protein III, tumor necrosis factor receptor type I, tumor necrosis factor receptor type II, urokinase-type plasminogen activator receptor, vascular endothelial growth factor, and chimeric proteins and biologically or immunologically active fragments thereof The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

7.2. ROUTES OF ADMINISTRATION

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

7.3. COMPOSITIONS/FORMULATIONS

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for limposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight. For compositions of the present invention which are useful for bone, cartilage, tendon, ligament, or other tissue regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the fracture repair activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), insulin-like growth factor (IGF), other known angiopoietins, VEGF, bone morphogenic protein (BMP), as well as other cytokines and/or growth factors described herein.

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

7.4. EFECTIVE DOSAGE

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

An exemplary dosage regimen for the human polypeptides of the invention will be in the range of about 0.01 to 100 mg/kg of body weight daily, with the preferred dose being about 0.1 to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

7.5. PACKAGING

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

8. ANTIBODIES

Another aspect of the invention is an antibody that specifically binds the polypeptide of the invention. Such antibodies include monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide of the invention. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for" indicates that the variable regions of the antibodies of the invention recognize and bind FGFAn-Hy polypeptides exclusively (i.e., able to distinguish an FGFAn-Hy polypeptide from other growth antagonist polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the FGFAn-Hy polypeptides of the invention are also contemplated, provided that the antibodies are first and foremost specific for, as defined above, FGFAn-Hy polypeptides. As with antibodies that are specific for full length growth factor antagonist polypeptides, antibodies of the invention that recognize FGFAn-Hy fragments are those which can distinguish FGFAn-Hy polypeptides from the family of growth factor antagonist polypeptides despite inherent sequence identity, homology, or similarity found in the family of proteins. Antibodies of the invention can be produced using any method well known and routinely practiced in the art.

Non-human antibodies may be humanized by any methods known in the art. In one method, the non-human CDRs are inserted into a human antibody or consensus antibody framework sequence. Further changes can then be introduced into the antibody framework to modulate affinity or immunogenicity.

Antibodies of the invention are useful for, for example, therapeutic purposes (by modulating activity of a polypeptide of the invention), diagnostic purposes to detect or quantitate a polypeptide of the invention, as well as purification of a polypeptide of the invention. Kits comprising an antibody of the invention for any of the purposes described herein are also comprehended. In general, a kit of the invention also includes a control antigen for which the antibody is immunospecific. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Research. 175:109–124 (1988)). Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and Sepharose®, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

9. COMPUTER READABLE SEQUENCES

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention. By providing the nucleotide sequence of SEQ ID NO: 1 or a representative fragment thereof, or a nucleotide sequence at least 99.9% identical to SEQ ID NO: 1 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

10. TRIPLE HELIX FORMATION

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself(antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

11. DIAGNOSTIC ASSAYS AND KITS

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample. In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. I (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

12. MEDICAL IMAGING

The novel polypeptides of the invention are useful in medical imaging, e.g., imaging the site of neovascularization. See, e.g., Kunkel et al. U.S. Pat. No. 5,413,778. Such methods involve chemical attachment of a labeling or imaging agent, administration of the labeled polypeptide to a subject in a pharmaceutically acceptable carrier, and imaging the labeled polypeptide in vivo at the target site.

13. SCREENING ASSAYS

Using the isolated proteins and polynucleotides of the invention, the present invention further provides methods of obtaining and identifying agents which bind to a polypeptide encoded by the ORF from a polynucleotide of the invention to a specific domain of the polypeptide encoded by a polypeptide of the invention. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In Synthetic Peptides, A User's Guide, W.H. Freeman, N.Y. (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulthydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

14. USE OF NUCLEIC ACIDS AS PROBES

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NO: 1. Because the corresponding gene is only expressed in a limited number of tissues, especially adult tissues, a hybridization probe derived from SEQ ID NO: 1 can be used as an indicator of the presence of RNA of cell type of such a tissue in a sample.

Any suitable hybridization technique can be employed, such as, for example, in situ hybridization. PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERITυ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search. Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology that were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLE 1

Cloning of Growth Factor Antagonist cDNA

Novel nucleic acids were obtained from various cDNA libraries (prepared from human mRNA purchased from Invitrogen, San Diego, Calif.) using standard PCR, sequencing by hybridization (SBH) sequence signature analysis and Sanger sequencing techniques. The inserts of the library were amplified with PCR using primers specific for pSport1 (GIBCO BRL, Grand Island, N.Y.) vector sequences which flank the inserts. These samples were spotted onto nylon membranes and hybridized with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to flourescent dye terminator cycle sequencing. Single pass gel sequencing was done using a 377 Applied Biosystems (ABI) sequencer.

Sequence analysis identified a polynucleotide encoding a novel polypeptides designated CG165. The 5' sequence was determined as described in Example 2. The contig encoding CG165 was deduced from numerous clones identified below in Table 1.

TABLE 1

| Library | No. Clones | Clone ID | Sequence ID |
|---|---|---|---|
| ABR006 (human adult brain) | 1 | 15566181 | RTA00003809R.c.06.2.P.Seq |
| | | | RTA00003809F.c.06.1.P.Seq |
| ABR008 (human adult brain) | 2 | 15767384 | RTA00002543F.a.22.2.P.Seq |
| | | | RTA00002543F.a.22.1.P.Seq |
| | | | RTA00002543F.a.22.4.P.Seq |
| | | 15172714 | RTA00002118F.b.13.1.P.Seq |
| | | | RTA00002765R.d.07.1.P.Seq |
| | | | RTA00003809R.b.20.2.P.Seq |
| | | | RTA00003809F.b.20.1.P.Seq |
| | | | RTA00003809F.b.23.1.P.Seq |
| | | | RTA00003809R.b.03.2.P.Seq |
| | | | RTA00003809R.b.23.2.P.Seq |
| | | | RTA00002765R.d.07.2.P.Seq |
| FBR006 (human fetal brain) | 1 | 15310267 | RTA00002833F.h.17.1.P.Seq |
| | | | RTA00002833F.h.17.2.P.Seq |
| FBRS03 (human fetal brain) | 1 | 25364534 | RTA00001747F.e.22.1.P.Seq |
| THMc02 (human adult thymus) | 1 | 16429685 | RTA00003219F.i.24.1.P.Seq |
| | | | RTA00003219F.i.24.2.P.Seq |
| | | | RTA00003219F.i.24.3.P.Seq |

EXAMPLE 2

5' RACE Extension of FGFAn-Hy Gene

5' RACE reactions were performed using two nested gene-specific primers (GSP) and vector primers (VP) in sequential PCR reactions on a panel of cDNA libraries. The cDNA libraries used for RACE were prepared from mRNA using a random-primed, 5' capture method to enrich for the 5' ends of genes (Carninci et al, Genomics, 37, 327–336, 1996) and cloned into the pSPORT vector (BRL Life Technologies) previously digested with NotI and SalI. The human mRNAs (Invitrogen) included message from adult brain, adult thymus, fetal muscle, fetal skin, fetal heart, fetal brain, fetal spleen, fetal liver, and fetal lung. In addition, adaptor-ligated cDNA pools (Marathon cDNAs, Clontech) made from human fetal kidney, fetal brain and adult ovary mRNAs were used in the RACE experiments.

The primers used are shown in Table 2 below. In the first reaction, GSP1 ($T_m$~80° C.) and VP1 ($T_m$~72° C.) were mixed in a 5:1 ratio. Touchdown PCR was carried out as follows: an initial incubation at 96° C. for one minute, followed by five cycles of 96° C. for 30 seconds and 72° C. for four minutes; five cycles of 96° C. for 30 seconds and 70°

C. for four minutes; and 15 cycles of 96° C. for 30 seconds and 68° C. for four minutes. The products of the first reaction were diluted 1:20 and used as template for the second reaction. Primers GSP2 and VP2 (both $T_m$~60° C.) were mixed in a 1:1 ratio and PCR was carried out as follows: an initial incubation at 96° C. for one minute; and 30 cycles of 96° C. for 30 seconds, 55° C. for 30 seconds, and 72° C. for 90 seconds. Final RACE products were separated and identified using agarose gel electrophoresis. Selected fragments were subcloned into a TA cloning vector and the inserts were sequenced. Sequences used to complete the 5' end of CG165 were obtained from the following cDNA sources: human fetal skin cDNA, human fetal brain cDNA and human fetal lung cDNA.

TABLE 2

| | |
|---|---|
| pSPORT VP1:<br>5'AGGCACCCCAGGCTTTACACTTTA 3' | SEQ ID NO: 8 |
| pSPORT VP2:<br>5'TTCCCGGGTCGACGATTTCGT 3' | SEQ ID NO: 9 |
| Marathon cDNA VP1:<br>5'CCATCCTAATACGACTCACTATAGGGC 3' | SEQ ID NO: 10 |
| Marathon cDNA VP2:<br>5'ACTCACTATAGGGCTCGAGCGGC 3' | SEQ ID NO: 11 |
| GSP1 (CG165RI):<br>5'GTCCGGGGGGATGCACACTCCTTGCATTT 3' | SEQ ID NO: 12 |
| GSP2 (CG165R2):<br>5'TGGACCACCTTGGGCTGGAT 3' | SEQ ID NO: 13 |

EXAMPLE 3

Tissue Expression Study

PCR Analysis

Gene expression of the human growth factor antagonists is analyzed using a semi-quantitative PCR-based technique. A panel of cDNA libraries derived from human tissue (from Clontech and Invitrogen) is screened with FGFAn-Hy specific primers to examine the mRNA expression of FGFAn-Hy in human tissues and cell types. PCR assays (For example, 94° C. for 30 sec., 58° C. for 30 sec., 72° C. for 30 sec., for 30 cycles) are performed with 20 ng of cDNA derived from human tissues and cell lines and 10 picomoles of the FGFAn-Hy gene-specific primers. The PCR product is identified through gel electrophoresis. Amplified products are separated on an agarose gel, transferred and chemically linked to a nylon filter. The filter is then hybridized with a radioactively labeled ($^{33}P\alpha$-dCTP) double-stranded probe generated from the full-length sequence using a Klenow polymerase, random prime method. The filters are washed (high stringency) and used to expose a phosphorimaging screen for several hours. Bands of the appropriate size indicate the presence of cDNA sequences in a specific library, and thus mRNA expression in the corresponding cell type or tissue.

Expression analysis can also be conducted using Northern blot techniques.

EXAMPLE 4

Chromosomal Localization Study

Chromosome mapping technologies allow investigators to link genes to specific regions of chromosomes. Chromosomal mapping is performed using the NIGMS human/rodent somatic cell hybrid mapping panel as described by Drwinga, H. L. et al., Genomics, 16, 311–314, 1993 (human/rodent somatic cell hybrid mapping panel #2 purchased from the Coriell Institute for Medical Research, Camden, N.J.). 60 ng of DNA from each sample in the panel is used as template, and 10 picomoles of the same FGFAn-Hy gene-specific oligonucleotides are used as primers in a PCR assay (for example, 94° C. for 30 sec., 58° C. for 30 sec., 72° C. for 30 sec., for 30 cycles). PCR products were analyzed by gel electrophoresis. The genomic PCR product is detected in a human/rodent somatic cell hybrid DNA containing a specific human chromosome.

EXAMPLE 5

Expression of Growth Factor Antagonists in E. Coli

SEQ ID NO: 1 is expressed in E. coli by subcloning the entire coding region into a prokaryotic expression vector. The expression vector (pQE16) used is from the QIAexpression® prokaryotic protein expression system (QIAGEN). The features of this vector that make it useful for protein expression include: an efficient promoter (phage T5) to drive transcription; expression control provided by the lac operator system, which can be induced by addition of IPTG (isopropyl-β-D-thiogalactopyranoside), and an encoded $His_6$ tag. The latter is a stretch of 6 histidine amino acid residues which can bind very tightly to a nickel atom. The vector can be used to express a recombinant protein with a $His_6$ tag fused to its carboxyl terminus, allowing rapid and efficient purification using Ni-coupled affinity columns.

PCR is used to amplify the coding region which is then ligated into digested pQE16 vector. The ligation product is transformed by electroporation into electrocompetent E. coli cells (strain M15[pREP4] from QIAGEN), and the transformed cells are plated on ampicillin-containing plates. Colonies are screened for the correct insert in the proper orientation using a PCR reaction employing a gene-specific primer and a vector-specific primer. Positives are then sequenced to ensure correct orientation and sequence. To express growth factor antagonist polypeptides, a colony containing a correct recombinant clone is inoculated into L-Broth containing 100 μg/ml of ampicillin, 25 μg/ml of kanamycin, and the culture was allowed to grow overnight at 37° C. The saturated culture is then diluted 20-fold in the same medium and allowed to grow to an optical density at 600 nm of 0.5. At this point, IPTG is added to a final concentration of 1 mM to induce protein expression. The culture is allowed to grow for 5 more hours, and then the cells are harvested by centrifugation at 3000×g for 15 minutes.

The resultant pellet is lysed using a mild, nonionic detergent in 20 mM Tris HCl (pH 7.5) (B-PER™ Reagent from Pierce), or by sonication until the turbid cell suspension turned translucent. The lysate obtained is further purified using a nickel containing column (Ni-NTA spin column from QIAGEN) under non-denaturing conditions. Briefly, the lysate is brought up to 300 mM NaCl and 10 mM imidazole and centrifuged at 700×g through the spin column to allow the His-tagged recombinant protein to bind to the nickel column. The column is then washed twice with Wash Buffer (50 mM $NaH_2PO_4$, pH 8.0; 300 mM NaCl; 20 mM imidazole) and is eluted with Elution Buffer (50 mM $NaH_2PO_4$, pH 8.0; 300 mM NaCl; 250 mM imidazole). All the above procedures are performed at 4° C. The presence of a purified protein of the predicted size is confirmed with SDS-PAGE.

EXAMPLE 6

Evaluation of Activities In Vitro and In Vivo

The activity of growth factor antagonist polypeptides of the invention is assayed by monitoring the effect of such polypeptides on the activity of various signal transduction pathways. One commercially available system for monitoring signal transduction is the Dual-Luciferase™ Reporter Assay System (Promega Corp., Madison, Wis.). Briefly, mammalian cells capable of responding to a growth factor (e.g., an FGF) are co-transfected with (1) a construct expressing the growth factor antagonist polypeptide to be tested (e.g., FGFAn-Hy, or an active fragment or an active fusion protein), (2) a first reporter construct utilizing a constitutive promoter (as a control for monitoring transfection efficiency), and (3) a second reporter construct that is dependent on a transcription factor or an enhancer element involved in the signal transduction pathway of interest (which serves to monitor the activity of one of several signal transduction pathways).

Various second reporter constructs are available in both cis- and trans-configurations (from, e.g., Stratagene, La Jolla, Calif.). The trans-configuration involves two constructs, and is used to monitor direct or indirect effects on signal transduction pathways which activate one of several transcription factors. Second reporter constructs for the following transcription factors are currently available from Stratagene: the Elk1 transcription factor for the mitogen-activated protein kinase (MAPK) signaling pathway, the c-Jun transcription factor for the c-Jun N-terminal kinase (JNK) signaling pathway, the CREB transcription factor for the cAMP-dependent kinase (PKA) signaling pathway, the CHOP transcription factor for the p38 kinase signaling pathway, and the c-Fos and ATF2 transcription factors. The cis-configuration is used to monitor direct or indirect effects on six different enhancer elements. Second reporter constructs for the following enhancer elements are currently available from Stratagene: AP-1, CRE, NF-kappaB, SRE, SRF and p53. Other similar set of constructs may be prepared to monitor other transcription factors and enhancer elements known in the art.

Comparison of the level of expression of the second reporter in response to different levels of growth factor antagonist polypeptide expression indicates the effect of hat growth factor antagonist polypeptide on the basal activity of the growth factor receptor pathway, i.e., indicates whether the growth factor antagonist decreases or increases signaling through the pathway. Optionally the growth factor itself (e.g., an FGF) can be added to the assay (either directly or via co-transfection of another construct encoding the growth factor, particularly if the growth factor is an intracellular protein) to determine the effects of the growth antagonist polypeptide on signal induction, i.e., whether the growth factor antagonist reduces or enhances growth factor signaling.

The growth factor antagonist polypeptide's effects on a number of different signaling pathways can be determined by using appropriate second reporter constructs. Comparison of its effects on different pathways will show specificity of the growth factor antagonist's biological effects.

In addition, this system can be used to screen libraries for small molecule drug candidates or lead compounds that disrupt or enhance the effects of the growth factor antagonist.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims. All references cited within the body of the instant specification are hereby incorporated by reference in their entirety.

What is claimed is:

1. A method for identifying a compound that binds to a polypeptide consisting essentially of SEQ ID NO: 2, comprising:
   a) contacting a compound with the polypeptide for a time period sufficient to form a polypeptide/compound complex; and
   b) detecting the complex, wherein detection of the complex indicates identification of a compound that binds to the polypeptide.

2. A method for identifying a compound that binds to a polypeptide consisting essentially of SEQ ID NO: 2, comprising:
   a) contacting a compound with the polypeptide for a time period sufficient to form a polypeptide/compound complex, wherein formation of the complex results in a detectable change in phenotype;
   b) detecting the change in phenotype, wherein the phenotype is selected from the group consisting of proliferation and angiogenesis; and wherein detection of the change in phenotype indicates identification of a compound that binds to the polypeptide.

* * * * *